(12) United States Patent
Soerensen et al.

(10) Patent No.: US 9,309,063 B2
(45) Date of Patent: Apr. 12, 2016

(54) PNEUMATIC TRANSPORT SYSTEM

(75) Inventors: Peter Moeller Soerensen, Jelling (DK); Daniel Blak, Roedkaersbro (DK)

(73) Assignee: Blak & Sørensen ApS, Bording (DK)

( * ) Notice: Subject to any disclaimer, the term of this patent is extended or adjusted under 35 U.S.C. 154(b) by 645 days.

(21) Appl. No.: 13/499,772

(22) PCT Filed: Sep. 30, 2010

(86) PCT No.: PCT/DK2010/050247
§ 371 (c)(1),
(2), (4) Date: Apr. 2, 2012

(87) PCT Pub. No.: WO2011/038739
PCT Pub. Date: Apr. 7, 2011

(65) Prior Publication Data
US 2012/0195698 A1    Aug. 2, 2012

(30) Foreign Application Priority Data
Oct. 2, 2009   (DK) .................................. 2009 70138

(51) Int. Cl.
*B65G 51/36*   (2006.01)
*B65G 51/02*   (2006.01)
*B65G 51/18*   (2006.01)

(52) U.S. Cl.
CPC ............... *B65G 51/02* (2013.01); *B65G 51/18* (2013.01)

(58) Field of Classification Search
USPC ............... 406/3, 10, 36, 67, 72, 84, 112, 145, 406/147, 151, 176; 700/230
See application file for complete search history.

(56) References Cited

U.S. PATENT DOCUMENTS

| 163,366 | A | * | 5/1875 | Dowd ................ B65G 53/4616 |
| | | | | 406/184 |
| 623,970 | A | * | 5/1899 | Batcheller .............. B65G 51/26 |
| | | | | 406/149 |
| 783,151 | A | * | 2/1905 | Stoddard ................ B65G 51/26 |
| | | | | 406/149 |
| 1,370,872 | A | * | 3/1921 | Amsler ..................... F23K 3/00 |
| | | | | 110/104 R |
| 2,890,913 | A | | 6/1959 | Miskel et al. |
| 3,627,231 | A | * | 12/1971 | Kalthoff ............................ 406/3 |
| 3,945,682 | A | | 3/1976 | Hoagland et al. |
| 3,980,024 | A | * | 9/1976 | Futer ............................... 406/93 |

(Continued)

FOREIGN PATENT DOCUMENTS

| CN | 1286202 A | 3/2001 |
| CN | 1522941 A | 8/2004 |

(Continued)

*Primary Examiner* — Joseph Dillon, Jr.
(74) *Attorney, Agent, or Firm* — Roberts Mlotkowski Safran & Cole, PC; David S. Safran

(57) ABSTRACT

A conveying system including at least one tube connection, at least one dispatch station and at least one receiver station, where items are conveyed by an airflow in the direction of the airflow in the pipe connection from a dispatch station to a receiver station. The new feature of a conveying system is that the tube connection has an inner cross-sectional area, preferably a circular cross-sectional area, with a size greater than the largest cross-sectional area of an item, and which is preferably provided with at least twice the cross-sectional area compared with the largest cross-sectional area of an item. Hereby is achieved the advantage that several items may be conveyed in the same tube connection at the same time, where these items are sent individually and successively, corresponding to one item being sent immediately after another.

7 Claims, 1 Drawing Sheet

(56) References Cited

U.S. PATENT DOCUMENTS

| | | | |
|---|---|---|---|
| 4,000,927 A * | 1/1977 | Sakamoto | B65G 51/01 406/109 |
| 4,336,872 A | 6/1982 | Noda et al. | |
| 4,946,317 A * | 8/1990 | Liu et al. | 406/46 |
| 5,725,124 A * | 3/1998 | Bustos et al. | 221/211 |
| 6,371,125 B1 * | 4/2002 | Schmidt | A24C 5/323 131/109.2 |
| 6,712,561 B1 * | 3/2004 | Valerino et al. | 406/197 |
| 7,424,340 B2 | 9/2008 | Owens | |
| 7,500,809 B2 * | 3/2009 | Menday et al. | 406/188 |
| 2002/0150432 A1 * | 10/2002 | Smith et al. | 406/188 |
| 2002/0197117 A1 * | 12/2002 | Balko | 406/13 |
| 2007/0173972 A1 * | 7/2007 | Owens | 700/232 |

FOREIGN PATENT DOCUMENTS

| | | |
|---|---|---|
| CN | 101389554 A | 3/2009 |
| CN | 101402419 A | 4/2009 |
| DE | 21 65 782 A1 | 7/1972 |
| EP | 0 511 093 A1 | 10/1992 |
| FR | 2 639 336 A1 | 5/1990 |
| GB | 1 182 418 A | 2/1970 |
| GB | 1 436 983 A | 5/1976 |
| GB | 2 411 635 A | 9/2005 |
| SU | 1006348 A | 3/1983 |

* cited by examiner

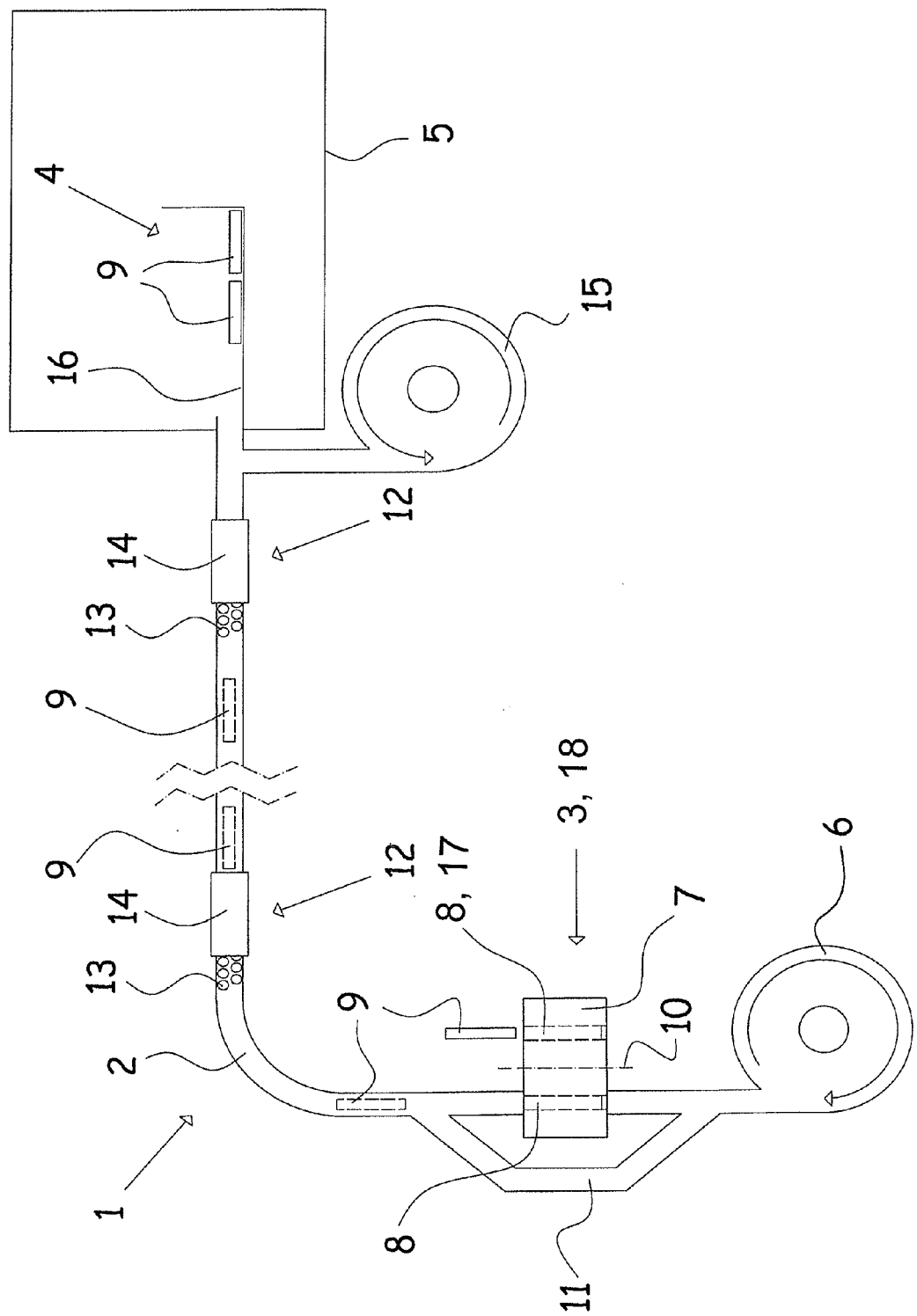

PNEUMATIC TRANSPORT SYSTEM

BACKGROUND OF THE INVENTION

1. Field of the Invention

The present invention concerns a conveying system suitable for conveying blood samples, including at least one tube connection with an internal cross-dimension/diameter/diagonal, at least one dispatch station and at least one receiver station, where items are conveyed by airflow in the direction of the airflow in the tube connection from a dispatch station to a receiver station. The invention also concerns the use of such a conveying system.

2. Description of Related Art

It is commonly known to use conveying systems with a number of tube connections wherein items are sent from a dispatch station to a receiver station by means of vacuum or pressurised air. Typically, an elongated capsule is sent which is provided with sealing rings at each end so that the cross-section of the tube connection is filled in this way. The capsule thereby acts as a plug which is conveyed in a long tube system. In the capsule there is typically provided the item to be transported to the desired destination. Such systems are known as so-called pneumatic dispatch systems and have been used for a long time in connection with internal post or similar in large buildings. However, by such systems there is the inexpediency that several items cannot be sent in immediate succession just like that. This is due to the fact that the systems are closed systems and that the capsule will stop underway in the tube connection if the closed system receives "false air". In order to be able to send capsules as quickly as possible in succession, various systems have been developed. One system may be provided with an indicator showing when a capsule is at the end station and thereby that the system is ready for use again. There are also other variants of pneumatic dispatch systems that are divided into different sections where each section is provided with its own vacuum or blowing mechanism. This allows for a new capsule to be sent as soon as the previously sent capsule has passed given positions in the tube connection.

However, such solutions all depend on the item to be conveyed to be put into a capsule and then to be dispatched. Also, it is necessary to take the item out of the capsule at the other end of the system. If approximately the same amount of capsules are sent both ways, the problem of an accumulated amount of capsules at a receiver station and a lacking amount of capsules at a dispatch station is solved, but in very few cases there will be a need for receiving capsules at respective dispatch stations, something which is not expedient. Such a system is known from U.S. Pat. No. 7,424,340 B2.

From FR 2 639 336 is known a solution where coins are conveyed in a tube connection with a cross-section greater than that of the coins. This kind of tube conveying system is possibly suited for some types of items, e.g. coins, by which a more or less chaotic transport of the items is allowable. In FR 2 639 336 it appears that coins are put in and conveyed without any further precautions, why such a system is not suited for conveying items where a certain control and guiding of the sent items is supposed and where they are to be received in a given order.

From U.S. Pat. No. 2,890,913 a system for conveying items such as vials is known. This system allows only one item to be in the system, as the system comprises a kind of turning point, where the item via a trap door is stopped and then by help of gravity falls into a receiving station. As this system only allows for one item to be in the system during a period of time, there is a need for having a signal for when it is possible to send the next item. Further the items are accelerated by a "shot" of pressurized air, and the item will be subject to quite a shock and a rough handling, as it is hit by the air. Such a system is troublesome due to the fact that it can only handle one item at a time and does not fulfil requirements to such a system nowadays.

From U.S. Pat. No. 3,945,682 another system is know, where more items can be conveyed together and successively. However this system concerns an opening where items are sucked in and send via a channel to a further process, where the items are turned end on end and resend. To help the sending of the items pressurized air can be used to move the items into the suction channel. There is used an airflow from two different sources and no constant airflow is provided. The part of the airflow from the suction is continuous, but as two different sources for providing the airflows are used, the items will experience a pulsating movement, which can have a negative influence on items that has to be transported without too much disturbance and jolting.

Further a system as seen in U.S. Pat. No. 3,945,682 will only work for moving items a relatively short distance as the continuous airflow that provides the suction and at the same time is the carrying medium for the items always will flow the way with the least resistance in the system of channels. When the channel system has a certain length and thus a corresponding friction and resistance the flow of air will only be in the wanted direction as long as there is no other way with less friction and resistance. This fact and the problem of such a system arises due to the system being an open system, where the continuous airflow is supplied to the channel system at a distance to the dispatch station, and sucking in ambient air at the dispatch station due to the common known ejector principle also known as the venturi effect. If a channel system of such a conveying system has a certain length or a certain numbers of items to convey the flow of air will turn and air will be pressed out of the dispatch station contrary to the intention with the system.

SUMMARY OF THE INVENTION

It is the purpose of the invention to indicate a solution for a conveying system similar to a pneumatic dispatch system, but where items may immediately be sent successively, and where there is no need for putting the item into a capsule before dispatching and where it is possible to perform controlled conveyance.

DESCRIPTION OF THE INVENTION

As indicated above, the invention concerns a conveying system where items via an airflow in a tube connection are conveyed in the direction of the airflow. A feature of a conveying system according to the invention is that the tube connection has an inner cross-sectional area, preferably a circular cross-sectional area, of a size greater than the largest cross-sectional area of an elongated item measured transversely of the longitudinal direction of the item, and which preferably is provided with at least twice the cross-sectional area compared with the largest cross-sectional area of the item, where the items have a length which is greater than the largest inner cross-dimension/diameter/diagonal. By such a solution it is possible to convey an item in the tube connection if there is an excess of air with a relatively small overpressure. By conducting a large amount of air through the tube system, the air may lift and convey the item over distances of several hundred meters. At the same time, there is achieved the advantage that several items may be conveyed in the same tube connection simultaneously as there is such an excess of air that it does not influence the efficiency of the system to an appreciable degree. As mentioned, it is possible to perform conveying of up to a plurality of items at a time where these items are sent individually and successively corresponding to one item being sent immediately after the other. A further advantage of a system as mentioned is that the items are sent with a certain orientation and that the items also arrive at a receiver station with the same orientation. Thus there is no need for staff to use time on turning items end on end before further dispatching or processing. This is a significant advantage since a receiver station may thus operate automatically more easily, thereby reducing the workload on the staff and the costs of the avoided sorting.

A conveying system according to the invention may be with a tube connection with an inner diameter which is about twice the diameter of the item to be transported. Of course this implies that the area of the item only constitutes ¼ of the area in the tube connection itself, having the consequence that there is ample air in the tube connection for conveying several items in the tube connection at the same time. The items may advantageously be sent one by one, whereby a certain distance between respective items is created. A typical item may e.g. be an elongated cylindric container with a diameter of 10-20 mm, or maybe with even larger thickness, and with a length of 75-150 mm, and the tube connection may advantageously be with an inner diameter of 20-50 mm. Items and tube connections with less as well as greater diameters/cross-sectional areas may be applied, and moreover there is no requirement that tube connection and/or items have circular cross-sections. However, it is required that the items are unable to be turned end on end during their conveying in the tube system why the largest inner cross-dimension, diameter, diagonal, side length or the like of the tube system cannot be greater than the length of an item.

In order to ensure a good and certain dispatching from a dispatch station, a conveying system according to the invention are arranged such that a dispatch station includes at least one connection for pressurized air, where a continuously airflow is supplied to the tube system, via the dispatch station and via said at least one connection, bypassing the dispatch station.

An unobstructed airflow is therefore always present for carrying the items that already are underway in the tube connection. At the same time, there will not occur any appreciable pressure drop or change of airflow at the dispatch of yet an item, since a large amount of air is constantly supplied around the dispatch station itself.

In an embodiment of a conveying system according to the invention, the conveying system may advantageously include a dispatch station which includes a holder for the at least one item, where the at least one item is placed in a cutout in this holder, where the cutout in the holder in connection with sending the item is displaced into the airflow in the tube connection and is flushed by an airflow, where the airflow is generated by a mechanical blower device. By such a dispatch station, items may be dispatched without opening for the airflow in the tube connection. Actually, the holder may be designed as a revolving drum with a number of cutouts that are brought into the airflow one by one. By such a solution, a large number of items may be dispatched in succession. By having a cutout in the airflow all the time, there is achieved the obvious advantage that the airflow is not disturbed substantially while at the same time a rapid dispatching of items may be effected.

The airflow may as mentioned be generated by a mechanical blower of suitable type, and as is mentioned above there is no need for a very great air pressure, why an overpressure of 1 bar will often be enough when there is a sufficient airflow and thereby airspeed in the tube connection. For the above mentioned dimensions of tube connections and items, an airflow between 100 and 300 $m^3$/hour will often be applied, somehow depending on the weight of the items and the sundry dimensions.

A conveying system according to the invention may advantageously be provided with a tube connection that further includes a mechanical suction device by which air is sucked and conducted away, where the air is sucked out immediately before a receiver station. Hereby is achieved the advantage that no overpressure is built up in the room in which the receiver station is established as the amount of air sucked out preferably at least corresponds to the amount of air supplied to the tube connection. This may e.g. be in a laboratory where it is not desired that air, possibly contaminated, is introduced. This security may be achieved by removing e.g. 10% more air at the receiver station than supplied from the dispatch station. This will also impart a decelerating action on the conveyed items, and thereby a more gentle reception of the latter is achieved.

A conveying system according to the invention may also be adapted such that the at least one tube connection of the conveying system is equipped with one or more regulators for the airflow, where the airflow regulators are provided with adjustable means for opening or closing apertures in the surface of the tube connection. Such an airflow regulator may advantageously be arranged immediately after a dispatch station, whereby it becomes possible to regulate the airflow down to a suitable level. The reason for this is that in order to accelerate the item in connection with dispatch from a dispatch station, an excess of air is usually applied. This excess air will impart high speed to the item, which, depending on the item, may be an advantage or a drawback. In the cases where the item is not to be subjected to high speed and thereby unnecessary jolting movements, an airflow regulator may be applied with advantage. Such a regulator of airflow may in its simplest form be provided as a displaceable member that opens or closes perforations in the tube connection. Such perforations may be holes or slots and may be with constant cross-sectional area implying a linear characteristic or with a varying cross-sectional area implying a non-linear characteristic on the regulator.

Other ways of regulating the airflow may be mechanical suction from the tube connection, but the effect will be the same and the speed of the item may be adjusted in this way. An airflow regulator may also be used with advantage for braking items prior to arrival at a receiver station.

The conveyor system according to the invention may be designed such that the at least one tube connection is made of tubing or hose, preferably of tubing or hoses of plastic or metal. These tubes or hoses may be used for vertical as well as horizontal and oblique mounting as the overpressure in the tube connection will ensure that the item is brought forward regardless of the direction of conveying being up, down or along. By using hoses with long length and with a certain flexibility, easy mounting with a minimum of joints in the tube connection is achieved. However, in connection with systems where the tube connection may be several hundred meters long, maybe up to 1000 m, for mounting reasons there are obviously to be a number of joints along the length. These joints are made with great care in order to avoid possible internal edges and/or displacements that may cause braking of items. Another important parameter is the surface roughness or the friction coefficient on the inner surface in the tube connection and on the item. Depending on the friction in the tube connection between the inner surface and the item, and the weight of the item, air pressure and airflow may be regulated to optimum.

A variant according to the invention may be where the conveying system further includes identification means, where these identification means are connected with a central data system. Thus it may be ensured that the dispatcher or that which is dispatched becomes registered whereby various forms of documentation may be provided. The central data system may advantageously be a computer system with programs suited and adapted therefor.

A conveying system according to the invention may advantageously be used for conveying items where the items are constituted by the material to be conveyed. Thus there is no need for putting the item into a special capsule adapted to be conveyed in the tube connection. Hereby is achieved the obvious advantage that the conveying system is easier and faster in use as no time is used in putting the item into a capsule and taking the item out of this capsule. At the same time there is no need to ensure the presence of available capsules at the dispatch stations.

A conveying system according to the invention may advantageously be used for conveying items constituted by containers, where a container contains e.g. a blood sample or other sample, wherein the item is conveyed from a dispatch station, and via the conveying system sent to a receiver station in connection with a laboratory. Such blood samples are taken and stored directly in a test tube-like container with cover and is typically made of clear plastic, e.g. polyethylene or polycarbonate. The blood samples are then sent from a dispatch station which preferably is placed close to a sampling site. Such a container is robust and suitable for transport in a conveying system according to the invention. However, it may be inexpedient that a blood sample is subjected to too many jolts, why it is advantageous to regulate the speed with a regulator for airflow with regard to the conveyed items.

By using a conveying system according to the invention, e.g. in a hospital for transporting blood samples from a location close to a sampling site and to a laboratory where the blood sample is to be examined more closely, a much faster processing time is attained since the sampler may continuously send the samples to closer examination and not, as normally, take out a number of samples and subsequently deliver all the samples collectively to the laboratory. As there are often long distances in a hospital, a conveying system according to the invention may be used with advantage since the transport of a blood sample can occur rapidly after which the sample can be examined correspondingly rapidly. At the same time there is the advantage that the tasks continuously come to the laboratory and therefore also may be analysed continuously, implying a markedly reduced consumption of resources.

In a variant of the invention, this may include a feeding system from which items to be dispatched one by one are automatically introduced in the dispatch station and thus just may be put into the said feeding system. In a preferred variant of such a system, the feeding system may include a number of magazines in which items are put, and where the filled magazines are subsequently placed in the feeding system in which the magazines are conveyed mechanically, and the individual items are actuated into a dispatch station. By such a solution, items may be provided in the said feeding system in a greater number at once, and the items may subsequently continuously be dispatched in the tube system. By such a feeding system there is achieved a more optimal utilisation of the capacity of the system as individual items are dispatched with optimal spacing, and placing of items in magazines or directly in a feeding system may occur in "lumps" as possibly a large number of items have been made ready for dispatch. By a feeding system as indicated here, the items may rapidly be placed, and dispatch may be effected subsequently without supervision by staff. The feeding system may be directly connected to the dispatch station, and items may be dispatched directly from the feeding system and/or the said magazines, but items may also be transferred from the feeding system or from a magazine to a holder connected to the dispatch station, the holder used in connection with dispatching items.

The invention is described in the following with reference to the drawing, wherein:

BRIEF DESCRIPTION OF THE DRAWING

The sole FIGURE shows schematically a conveying system.

DETAILED DESCRIPTION OF EMBODIMENTS OF THE INVENTION

In FIGURE shows a conveying system 1 according to the invention shown schematically, where the conveying system 1 includes a tube connection 2 which extends from a dispatch station 3 to a receiver station 4 in a closed room 5. Under the dispatch station 3 appears a blower 6 from where a sufficient amount of air is blown into the tube connection 2. The air is conducted through the dispatch station 3 which is provided with a revolving drum 7 in which are arranged a number of holders in the shape of cutouts 8. An item 9 may be placed in these cutouts 8, and by rotating the revolving drum 7 about its centre axis 10, the cutouts 8 may be brought one by one into the airflow present in the tube connection 2. In order to ensure a sufficient excess of air in the tube connection 2, a constant airflow is conducted around the dispatch station 3 via a bypass duct 11 by which it is ensured that items 9 underway in the tube system 2 remain moving.

Immediately after dispatching the item 9 from the dispatch station 3, the speed of the item 9 may be regulated by an airflow regulator 12 which in all simplicity operates by discharging a part of the air through apertures 13 in the tube system 2. The speed of the item 9 is hereby reduced after being accelerated to a suitable speed after the dispatch station 3. In the shown embodiment of the airflow regulator 12, there are apertures 13 in the tube connection 2 which may be covered more or less by a displaceable part 14. In order to further reduce the speed of the item 9 before the item 9 arrives at the receiver station 4, in the shown conveying system there is depicted yet an airflow regulator 12, and also a suction device 15 by which air can be removed. Both airflow regulator 12 and suction device 15 may contribute to draft and overpressure not occurring in the closed room 5 which e.g. can be a laboratory. By closing and removing part of the air with the airflow regulator 12 and even more by the suction device 15, the item 9 may be decelerated to such a degree that the item 9 comes to rest in a delivery tray 16. When the suction device 15 removes more air than what is present in the tube connection 2, a small part of the air in the closed room 5 is removed automatically. Hereby may be ensured that contaminated air is not supplied to the closed room 5 which may be very important in connection with a receiver station 4 being arranged in a laboratory 5.

The invention is not limited to the above described embodiments or as shown in the drawing, but may be supplemented and adapted in various ways within the scope of the invention as defined by the claims.

The invention claimed is:

1. A conveying system for conveying samples, including at least one elongated item for holding the samples, a tube system having at least one tube connection with an internal cross-sectional dimension, at least one dispatch station for dispatching the at least one elongated item into a path, at least one receiver station for receiving the at least one elongated item dispatched into said path, and an air conveying device which is positioned for producing an airflow in the tube connection in a direction along said path from the dispatch station to to the at least one receiver station, where the inner cross-sectional area of the tube connection is of a size greater than the largest cross-sectional area of the at least one elongated item to be conveyed along said path measured transversely of the longitudinal direction of the item, and which is provided with at least twice the cross-sectional area compared with the largest cross-sectional area of the item, where the items have a length which is greater than the largest inner cross-sectional dimension, where the air conveying device includes at least one connection for supplying pressurized air to the at least one dispatch station, wherein said air conveying device also includes at least one connection for supplying pressurized air to a bypass duct, said bypass duct being configured and arranged extending around the at least one dispatch station from an upstream to a downstream side thereof for enabling a constant airflow to be conducted around the at least one dispatch station into said path by which items already underway along said path in the tube system remain moving during dispatching of an item into said path.

2. A conveying system according to claim 1, wherein the dispatch station in the conveying system includes a holder for the at least one item, where the holder has at least one cutout by which the at least one item is insertable into the holder, where the cutout in the holder is flushed by an airflow generated by a mechanical blower device for displacing the at least one item into the airflow.

3. A conveying system according to claim 1, wherein the tube connection includes a mechanical suction device by which air is sucked and conducted away, where the air is sucked out immediately before the at least one receiver station.

4. A conveying system according to claim 1, wherein the at least one tube connection of the conveying system is equipped with one or more regulators for the airflow, where the airflow regulators are provided with adjustable means for opening or closing apertures in the surface of the tube connection.

5. A conveying system according to claim 1, wherein the at least one tube connection is made of at least one plastic or metal tubing or hose.

6. A conveying system according to claim 1, wherein the conveying system further includes identification means, where these identification means are connected with a central data system.

7. A conveying system according to claim 1, wherein the conveying system further includes a feeding system wherein the feeding system includes at least one magazine for placing items, where the feeding system includes means for actuating the at least one magazine and means for actuating items in the at least one magazine, whereby items are moved from the feeding system and into the at least one dispatch station.

* * * * *